US011000400B2

United States Patent
Grum-Schwensen et al.

(10) Patent No.: US 11,000,400 B2
(45) Date of Patent: May 11, 2021

(54) RETRACTABLE OUTLET FOR OSTOMY POUCH

(71) Applicant: Hollister Incorporated, Libertyville, IL (US)

(72) Inventors: Christen Grum-Schwensen, Hillerod (DK); Jan Torstensen, Virum (DK); Mette Dybendal Maack, Lyngby (DK); Kenneth Nielsen, Alsgarde (DK); Sussie Richmann, Hellebaek (DK); Jan Wohlgemuth, Horsholm (DK); Peter Moller-Jensen, Hornbaek (DK); Ole Skjodt, Rungsted Kyst (DK)

(73) Assignee: Hollister Incorporated, Libertyville, IL (US)

( * ) Notice: Subject to any disclaimer, the term of this patent is extended or adjusted under 35 U.S.C. 154(b) by 363 days.

(21) Appl. No.: 16/071,044

(22) PCT Filed: Jan. 31, 2017

(86) PCT No.: PCT/US2017/015727
§ 371 (c)(1),
(2) Date: Jul. 18, 2018

(87) PCT Pub. No.: WO2017/136304
PCT Pub. Date: Aug. 10, 2017

(65) Prior Publication Data
US 2019/0029868 A1     Jan. 31, 2019

Related U.S. Application Data

(60) Provisional application No. 62/291,912, filed on Feb. 5, 2016.

(51) Int. Cl.
*A61F 5/445* (2006.01)
*A61F 5/44* (2006.01)

(52) U.S. Cl.
CPC ............ *A61F 5/445* (2013.01); *A61F 5/4407* (2013.01)

(58) Field of Classification Search
CPC .... A61F 5/4404; A61F 5/4405; A61F 5/4407; A61F 5/445
See application file for complete search history.

(56) References Cited

U.S. PATENT DOCUMENTS 3,523,534 A    8/1970   Nolan
4,411,659 A   10/1983   Jensen
(Continued)

FOREIGN PATENT DOCUMENTS

JP      3131250 U      4/2007
WO   2013142577 A1    9/2013

OTHER PUBLICATIONS

International Preliminary Report on Patentability issued by International Bureau in connection with PCT/US2017/015727 dated Aug. 16, 2018.
(Continued)

*Primary Examiner* — Susan S Su
(74) *Attorney, Agent, or Firm* — Levenfeld Pearlstein, LLC

(57) ABSTRACT

A drainable ostomy pouch (10) includes a collection pouch (12) having a collection cavity (20), a retractable outlet (14) movable between a first position retracted substantially into the collection cavity and a second position extending outwardly from the collection cavity, a discharge opening (30) formed at a distal end of the retractable outlet and a closure (22) configured to selectively allow or prevent discharge of a waste material from the collection cavity or the retractable outlet.

16 Claims, 16 Drawing Sheets

(56) References Cited

U.S. PATENT DOCUMENTS

| | | | |
|---|---|---|---|
| 7,879,015 B2 | 2/2011 | Villefrance et al. | |
| 8,672,907 B2 | 3/2014 | Friske et al. | |
| 9,011,395 B2 | 4/2015 | Friske et al. | |
| 2003/0028160 A1 | 2/2003 | Leise et al. | |
| 2003/0198704 A1* | 10/2003 | Blum | A61F 5/4407 425/172 |
| 2008/0262446 A1* | 10/2008 | Ryder | A61F 5/445 604/317 |
| 2009/0209926 A1* | 8/2009 | Cochran | A61F 5/445 604/332 |
| 2011/0028923 A1* | 2/2011 | Murray | A61F 5/4405 604/332 |
| 2011/0028924 A1* | 2/2011 | Murray | A61F 5/4407 604/332 |
| 2012/0022478 A1* | 1/2012 | Friske | A61F 5/4407 604/335 |
| 2012/0130329 A1* | 5/2012 | March | F16K 3/24 604/332 |
| 2013/0253455 A1* | 9/2013 | Masters | A61F 5/445 604/332 |
| 2013/0253456 A1 | 9/2013 | Friske et al. | |
| 2014/0194843 A1* | 7/2014 | Masters | A61F 5/4405 604/333 |
| 2014/0371699 A1* | 12/2014 | Feingold | A61F 5/442 604/334 |
| 2017/0156918 A1* | 6/2017 | Schertiger | A61F 5/448 |
| 2017/0189222 A1* | 7/2017 | Lin | A61F 5/4553 |
| 2018/0333290 A1* | 11/2018 | Jones | A61F 5/4407 |

OTHER PUBLICATIONS

International Search Report issued by ISA/EPO in connection with PCT/US2017/015727 dated Apr. 28, 2017.

Written Opinion issued by ISA/EPO in connection with PCT/US2017/015727 dated Apr. 28, 2017.

* cited by examiner

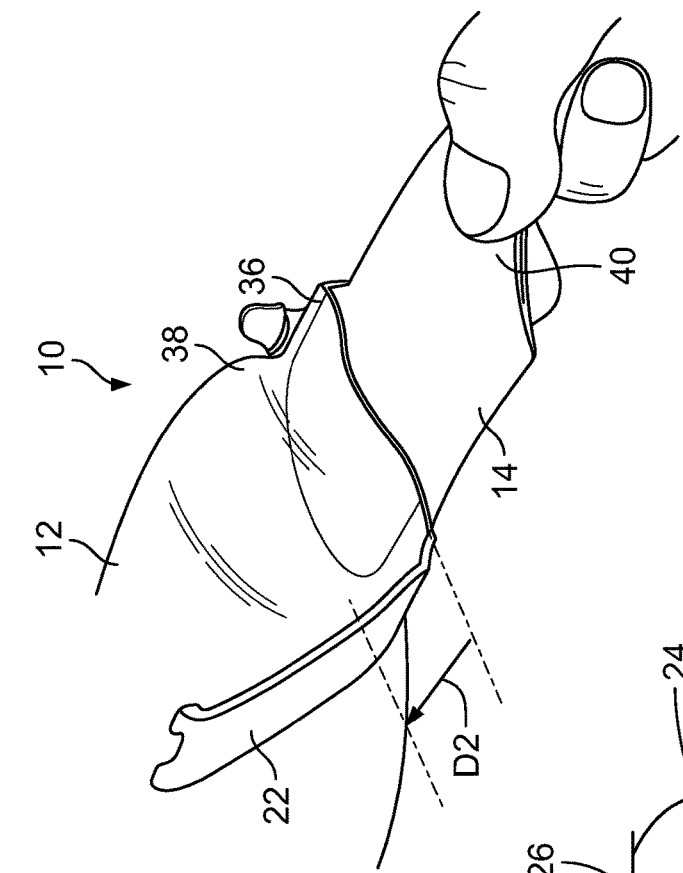
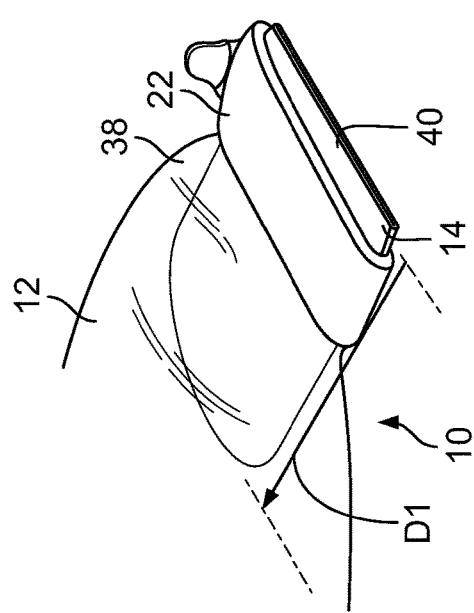
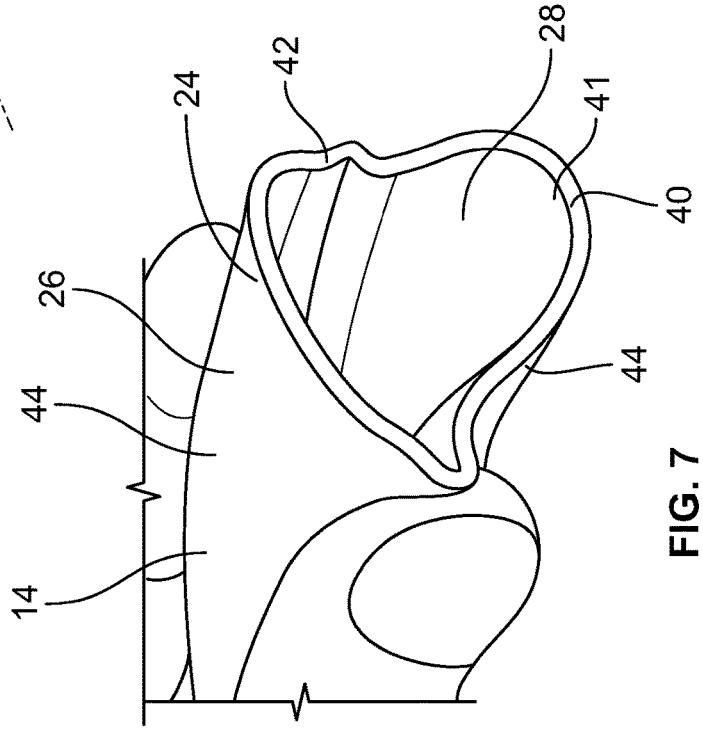
FIG. 5
FIG. 6
FIG. 7

RETRACTABLE OUTLET FOR OSTOMY POUCH

BACKGROUND

The following description generally relates to ostomy appliances, and in particular, drainable ostomy pouches having a retractable outlet section.

Ostomy pouches for collecting bodily waste are used by patients who have had surgery such as colostomy, ileostomy, or urostomy. Ostomy pouches typically include flat, opposing side walls secured together along their edges to define a collection cavity. One of the side walls is provided with an opening to receive a stoma, and means to secure the pouch to the user, such as an adhesive barrier, so that bodily waste discharged through the stoma is received within the cavity.

The ostomy pouch may be a drainable pouch having a discharge opening at a lower end. The discharge opening may be closed during collection of bodily waste material, but may be opened to drain the waste material from the pouch. Such drainable ostomy pouches are disclosed, for example, in Nolan, U.S. Pat. No. 3,523,534, and Jensen et al., U.S. Pat. No. 4,411,659, which are incorporated herein by reference in their entirety.

The discharge opening of drainable ostomy pouches is typically defined at the end of a narrowed neck portion, which provided with closure means for maintaining the discharge opening in a sealed condition until waste material is to be drained from the pouch. The closure means may take the form of a clamp, as in the aforementioned Nolan patent, or a device such as conventional wire tires or wraps for securing the neck portion in an upwardly-rolled condition.

For quality of life of the users or patients, drainable pouches should be easy to drain without risking soiling of clothes or the surroundings. The drainable pouches should also be easy to close securely after being drained and amenable to being cleaned after drainage and before closing again, such that the risk of unpleasant odor is substantially reduced. The closure means should also provide a secure seal when closed to minimize risk of waste leakage from the pouch.

Different solutions have been proposed with respect to the closing, cleaning and drainage operations. For example, Villefrance et al., U.S. Pat. No. 7,879,015, Friske et al., U.S. Pat. No. 8,672,907, and Friske et al. U.S. Pat. No. 9,011,395, which are commonly assigned with the present application and incorporated herein by reference in their entirety, disclose drainable pouches having integral closure systems. However, further improvements in closure systems for easier operation and cleaning, and reduced risk of leakage are desired.

Accordingly, it is desirable to provide a drainable ostomy pouch having a retractable outlet movable between a first, retracted position and a second, extended position, where in the second position, the outlet may be in a first state where waste may be received therein from the coupling area to exit the pouch, and a second state where the outlet is sealed off the from the pouch to allow for cleaning.

SUMMARY

According to one embodiment, there is provided an ostomy pouch having a collection pouch including a first side wall and a second side wall joined along a periphery to define an internal collection cavity, a retractable outlet movable between a first position retracted substantially into the internal collection cavity and a second position extending outwardly from the periphery, a discharge opening formed at a distal end of the retractable outlet, and a closure member configured to selectively allow or prevent discharge of a waste material from the collection cavity or the retractable outlet.

According to another embodiment there is provided a drainable ostomy pouch having a pouch body with a waste collection cavity defined therein, a first discharge opening disposed at one end of the pouch body, a retractable outlet fluidically connected to the pouch body via the first discharge opening, the retractable outlet having a second discharge opening, a first closure for closing the first discharge opening, and a second closure for closing the second discharge opening. The retractable outlet is retractable to a position within the collection cavity through the first discharge opening.

According to still another embodiment, there is provided a drainable ostomy pouch having a pouch body having a waste collection cavity defined therein and a first closure and a retractable outlet movable between a first position within the waste collection cavity and a second position extending from the waste collection cavity. The retractable outlet includes a discharge opening for draining contents from the collection cavity and a second closure for selectively closing the discharge opening.

Other objects, features, and advantages of the disclosure will be apparent from the following description, taken in conjunction with the accompanying sheets of drawings, wherein like numerals refer to like parts, elements, components, steps, and processes.

BRIEF DESCRIPTION OF THE DRAWINGS

FIG. 5 is a perspective view showing a portion of an ostomy pouch with a retractable outlet in a first position according to an embodiment described herein;

FIG. 6 is a perspective view of the ostomy pouch of FIG. 5 with the outlet in a second position;

FIG. 7 is a perspective view of a retractable outlet in an open condition according to an embodiment described herein;

DETAILED DESCRIPTION

Figure 1:
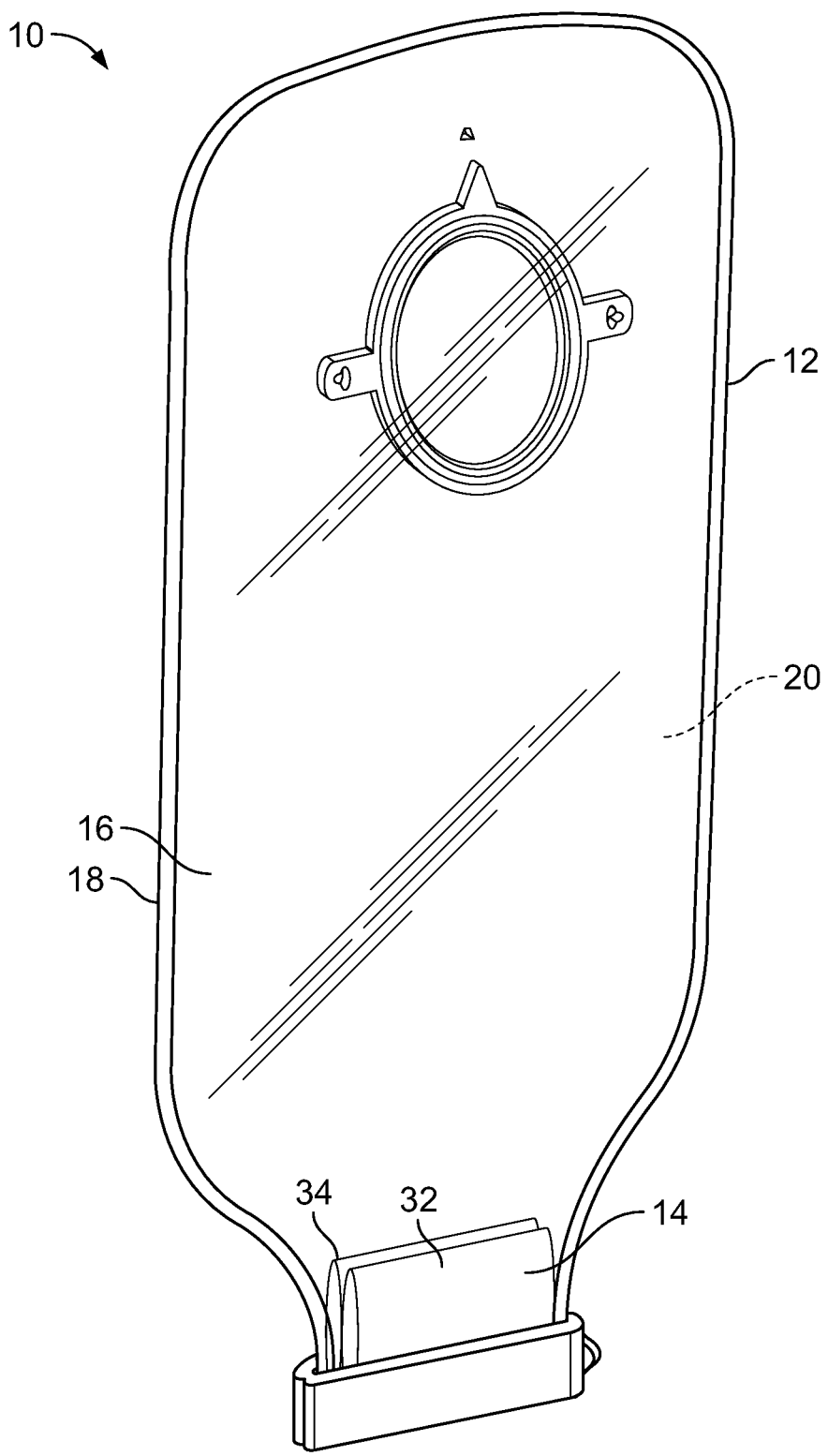
FIG. 1 is a perspective view showing a portion of an ostomy pouch with a retractable outlet in a first position according to an embodiment described herein.

While the present disclosure is susceptible of embodiment in various forms, there is shown in the drawings and will hereinafter be described one or more embodiments with the understanding that the present disclosure is to be considered illustrative only and is not intended to limit the disclosure to any specific embodiment described or illustrated.

Figure 2:
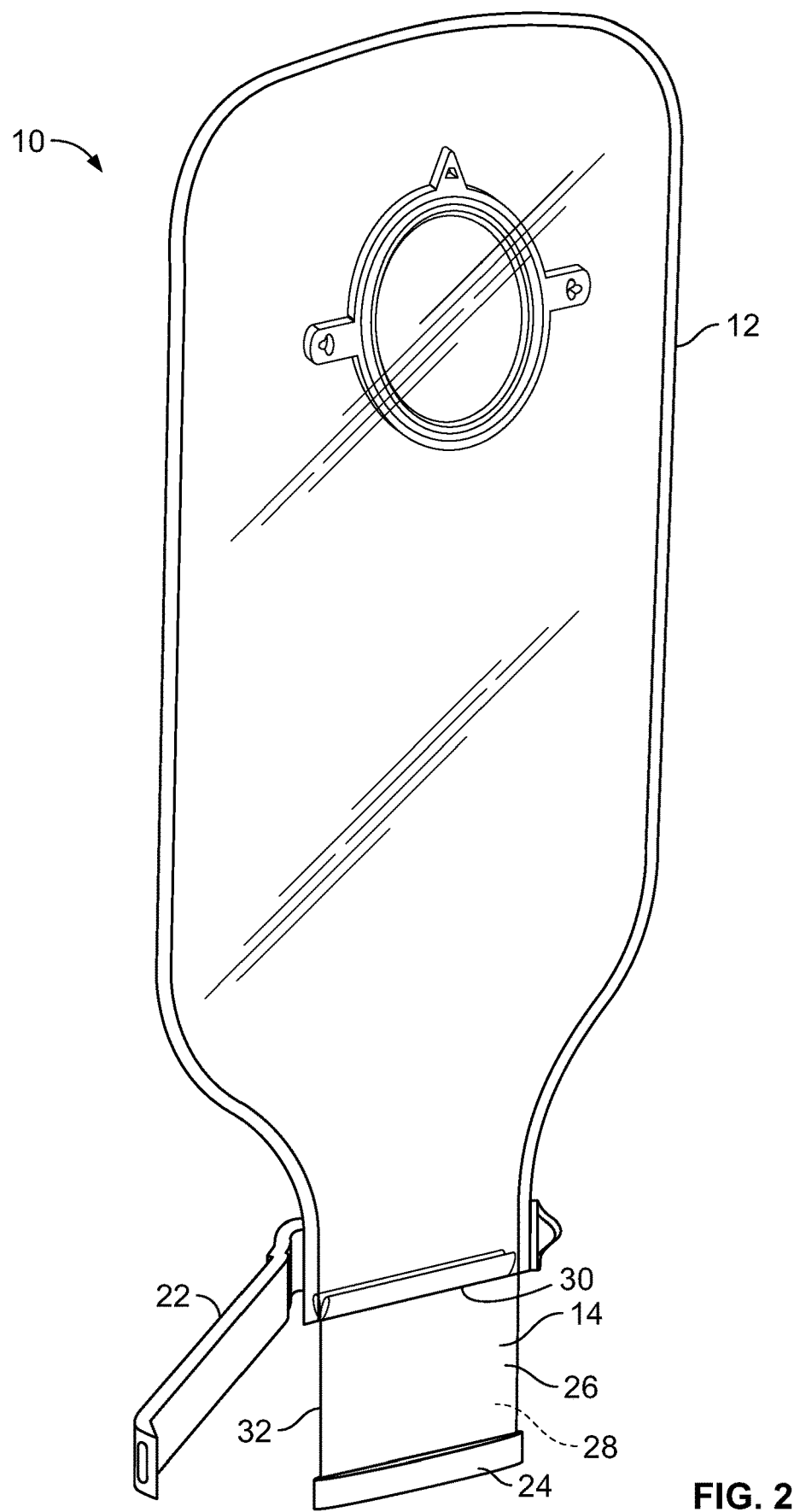
FIG. 2 is a perspective view of the ostomy pouch of FIG. 1 with the outlet in a second position.
Figure 3:
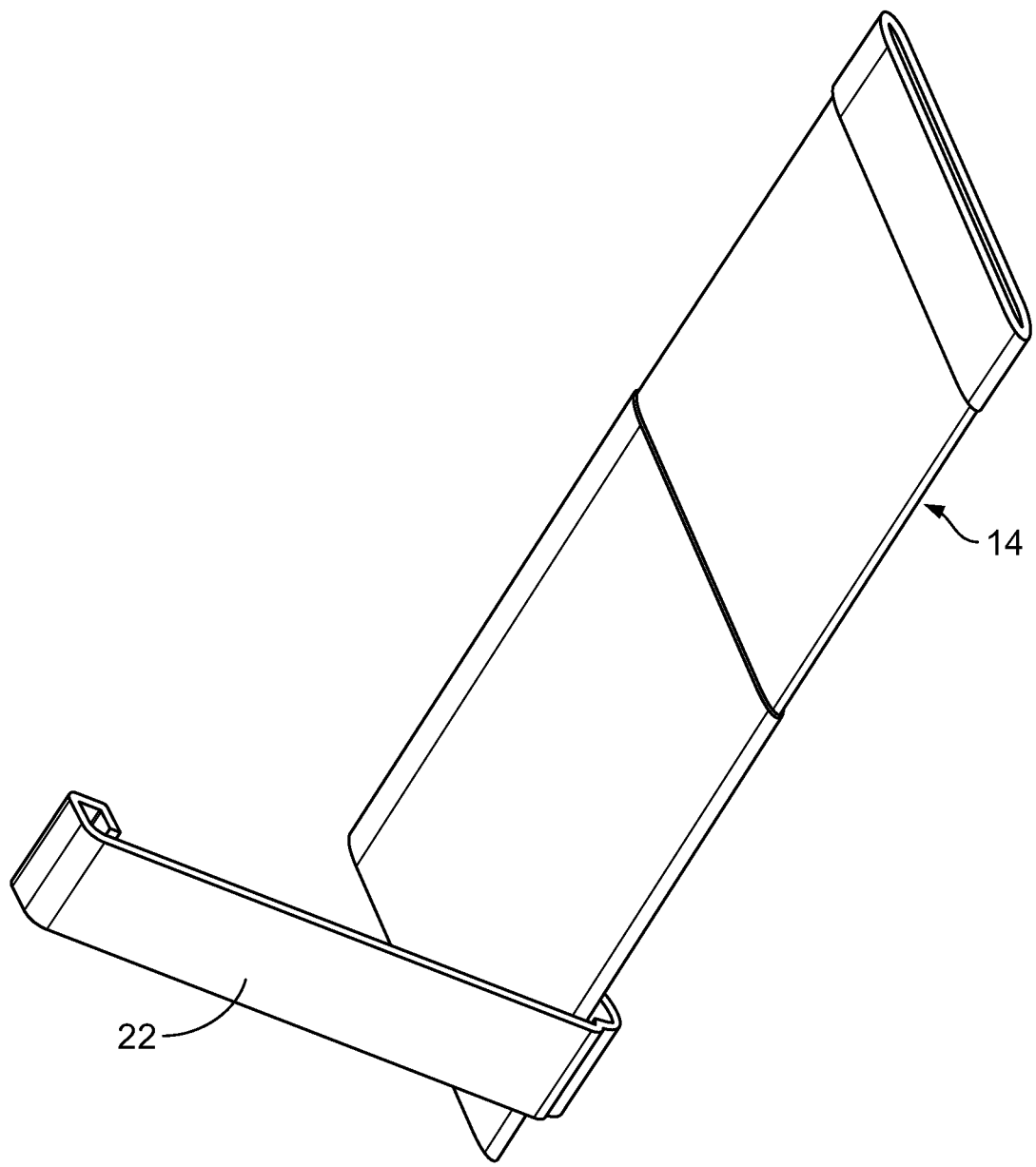
FIG. 3 is a perspective view of an ostomy pouch having a retractable outlet according to an embodiment described herein.
Figure 4:
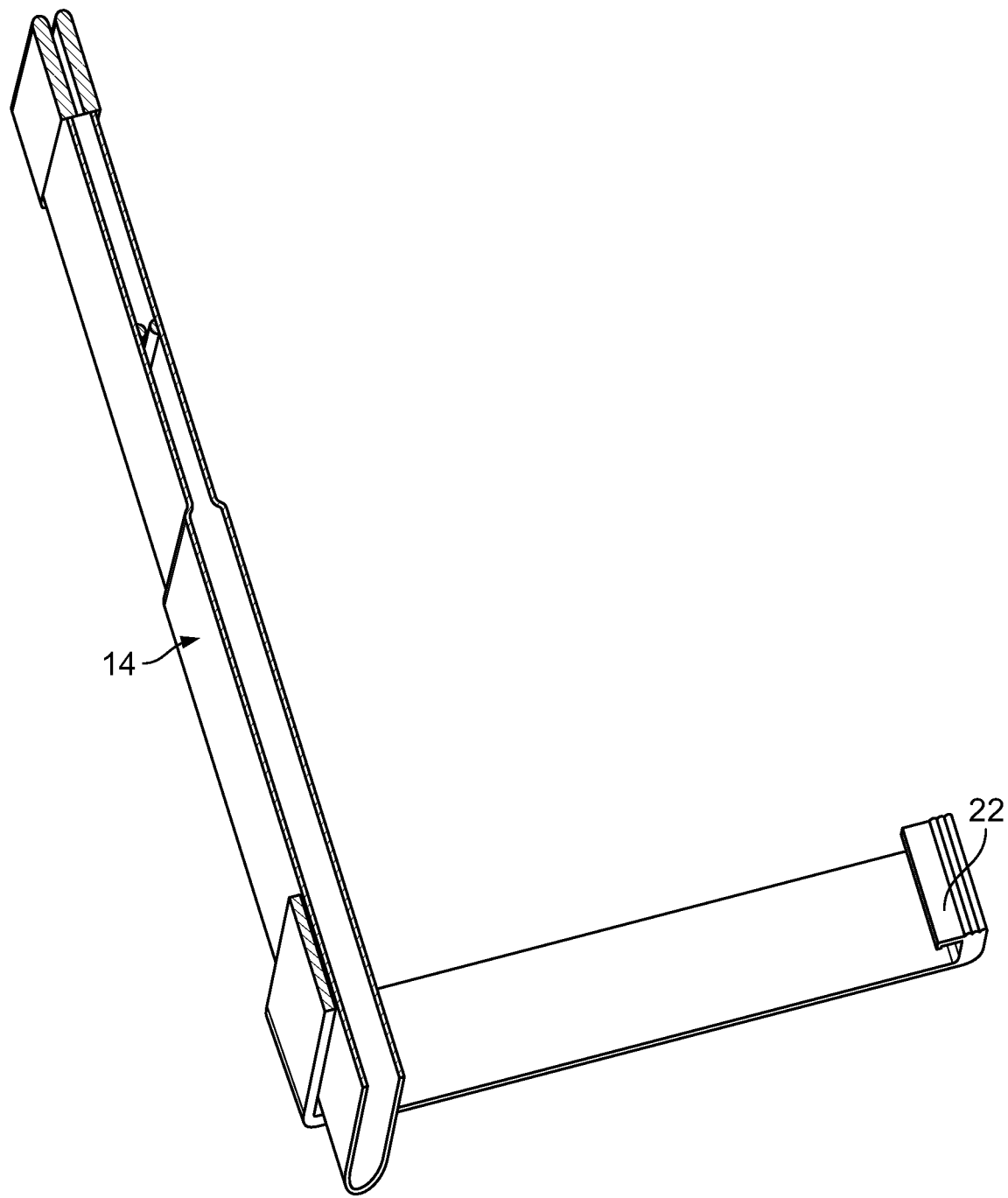
FIG. 4 is another perspective view of an ostomy pouch having a retractable outlet according to an embodiment described herein.

With reference to FIGS. 1-4, an ostomy pouch 10, according to the embodiments described herein, generally includes a collection pouch 12 and a retractable outlet 14 movable between a first, retracted position (FIG. 1) and a second, extended position (FIG. 2). The collection pouch 12 may generally be formed by a first side wall 16 and a second side wall 18 joined to one another at a periphery, or connected integrally with one another as a single unit. The collection pouch 12 includes an inlet (not shown) in one of side walls 16, 18 configured to receive a stoma. A collection cavity 20 is defined within the collection pouch 12, i.e., between the first and second side walls 16, 18. The retractable outlet 14 is retractable into and extendable outward from the collection cavity 20. The ostomy pouch 10 further includes a closure configured to selectively allow or prevent discharge of a waste material or other contents from collection pouch 12 or the retractable outlet 14. In one embodiment, the closure is a first closure 22 positioned on the collection pouch 12 so as to selectively close the collection cavity 20 and substantially prevent leakage of the contents from the collection cavity 20. The closure may alternatively be formed as a second closure 24 positioned on the retractable outlet 14 so as to selectively close the retractable outlet 14 and substantially prevent leakage of the contents from the retractable outlet 14. In another embodiment, the ostomy pouch 10 includes both the first closure 22 and the second closure 24.

In one embodiment, the retractable outlet 14 is formed, in part, by a wall 26, such as a single, continuous wall, or two or more walls secured and sealed together. The retractable outlet 14 includes an internal passageway 28 connected to the collection cavity 20 via a first discharge opening 30. In one embodiment, the first discharge opening 30 is formed as an opening in the periphery of the collection pouch 12. The retractable outlet wall 26 is reversible, i.e., invertible, as the retractable outlet 14 is moved from the first position to the second position, and vice versa. For example, in the first position, a first side 32 of the retractable outlet wall 26 faces generally outward and is in direct communication with the collection cavity 20, including any contents of the collection cavity 20. In the first position, the retractable outlet 14 forms a non-return valve substantially prevent leakage of the waste material or contents from the collection cavity 20. As the retractable outlet 14 is moved to the second position, the outlet wall 26 folds over itself at a bend 34 so the first side 32 of the outlet wall 26 faces generally inward. With the retractable outlet 14 in the second position, the first side 32 of the retractable outlet wall 26 faces generally inward and is in direct communication with internal passageway 28 of the retractable outlet 14. Accordingly, in the second position, the retractable outlet 14 may receive contents from the collection cavity 20 in the internal passageway 28.

FIG. 5 is a perspective view of an ostomy pouch 10 having the retractable outlet 14 in the first, retracted position. As shown in FIGS. 5 and 6, in one embodiment, the collection pouch 12 may include a neck 36 at one end, formed of a reduced width relative to a body 38 of the collection pouch 12. The retractable outlet 14 may be connected to the neck 36 and extend within the neck 36, at least in the first, retracted position. In one embodiment, the first closure 22 extends around the collection pouch 12, for example, at the neck 36, to selectively close and/or seal the collection pouch 12, thereby preventing or limiting unintentional flow of contents, e.g., bodily waste, from the collection pouch 12.

Referring still to FIG. 5, with the retractable outlet 14 in the first position, the first closure 22 may also close or seal the retractable outlet 14. Further, with the retractable outlet 14 in the first position, a portion of the retractable outlet 14 may extend outwardly from the collection pouch 12 to serve as a grip 40 for a user to move the retractable outlet 14 from the first position to the second position and vice versa. In the first position, the retractable outlet 14 extends a first distance D1 into the collection cavity 20 of the collection pouch 12.

FIG. 6 shows the retractable outlet 14 in the second position, extending from the collection pouch 12. In the second position, the retractable outlet 14 may extend a second distance D2 into the collection pouch 12, the second distance D2 being less than the first distance D1. In some embodiments, however, the retractable outlet 14 may extend completely from the collection pouch 12, i.e., does not extend into the collection pouch 12, in the second position. The retractable outlet 14 may be moved to the second position when the first closure 22 is in an open condition.

FIG. 7 shows the retractable outlet 14 in an open condition, according to an embodiment described herein. In one embodiment, the second closure 24 may be formed by a spring force in the retractable outlet 14 to selectively close and/or seal a second discharge opening 41 formed at an end of the internal passageway 28. For example, second closure 24 may be positioned at a distal end 42 of the retractable outlet 14, and the outlet 14 may be biased to close on itself and may seal the internal passageway 28 at the distal end 42. In one configuration, the outlet wall 26 may be formed of a resilient or elastic material and have opposed wall sections 44. The wall sections 44 may be shaped such that each wall section 44 is urged toward the other wall section 44 under an internal spring force of the material. Other configurations may include a spring, such as a leaf spring, externally or internally disposed with the wall sections 44 to urge the opposed wall sections 44 toward one another. The second closure 24 may be opened, for example, by exerting internally directed forces on opposed lateral edges of the outlet 14, for example, at the grip 40, to move the opposed wall sections 44 away from one another against the spring force. In other embodiments, the second closure 24 may be a releasable fastener understood to those having skill in art, which in a closed condition closes and may seal the distal end 42 of the retractable outlet 14, and in an open condition opens the distal end 42 of the retractable outlet 14.

Figure 9:
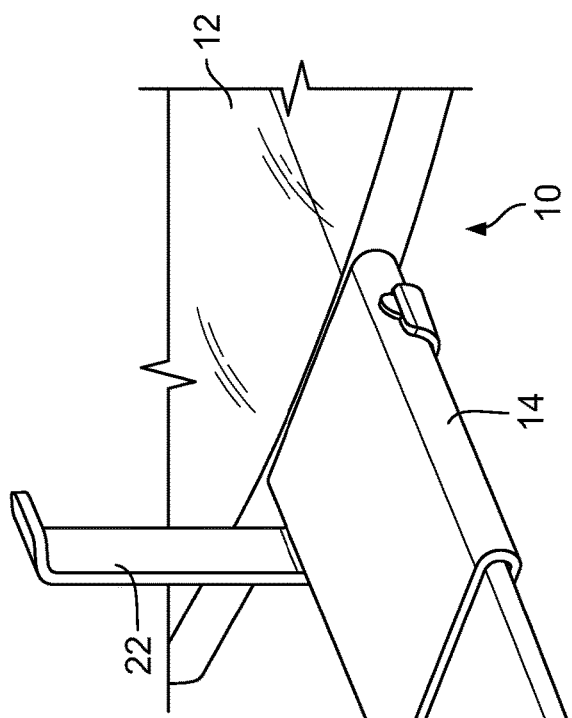
FIG. 9 is a perspective view showing the retractable outlet of FIG. 8 in a second position.
Figure 8:
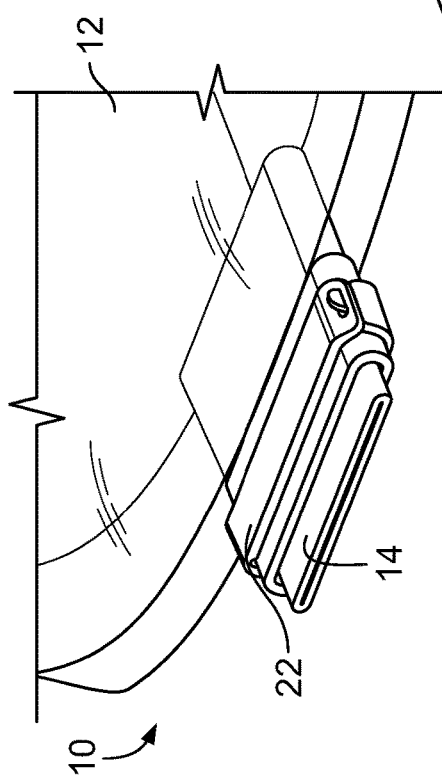
FIG. 8 is a perspective view showing the retractable outlet of FIG. 7 in a first position according to an embodiment described herein.
Figure 10:
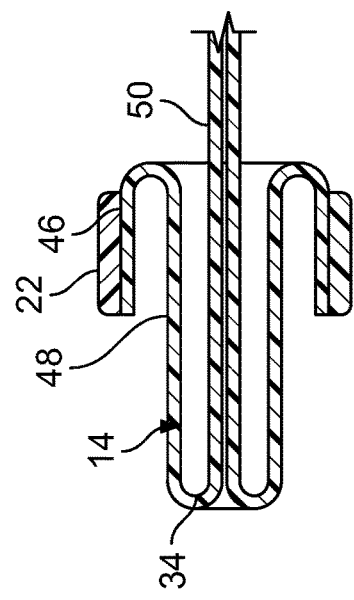
FIG. 10 is a cross-sectional view of the retractable outlet of FIGS. 8 and 9.

FIGS. 8 and 9 show a retractable outlet 14 in the first position (FIG. 8) and the second position (FIG. 9) according to an embodiment described herein. FIG. 10 shows a cross-section of the retractable outlet 14 of FIGS. 8 and 9. Referring to FIGS. 8-10, in one embodiment, the retractable outlet 14 may be formed in a three-layer configuration at or near a position of the first closure 22. In the three-layer configuration, a first, outer layer 46 may be secured to the collection pouch 12. A second layer 48 may extend from the first layer 46 into the collection pouch 12 in the first position. A third layer 50 extends outwardly from the collection pouch 12. The first, second and third layers 46, 48, 50 may be integrally and continuously formed, or formed separately and secured together using known fastening techniques such as heat sealing or welding. The outlet 14 may be folded over itself at bend or fold 34.

Figure 12:
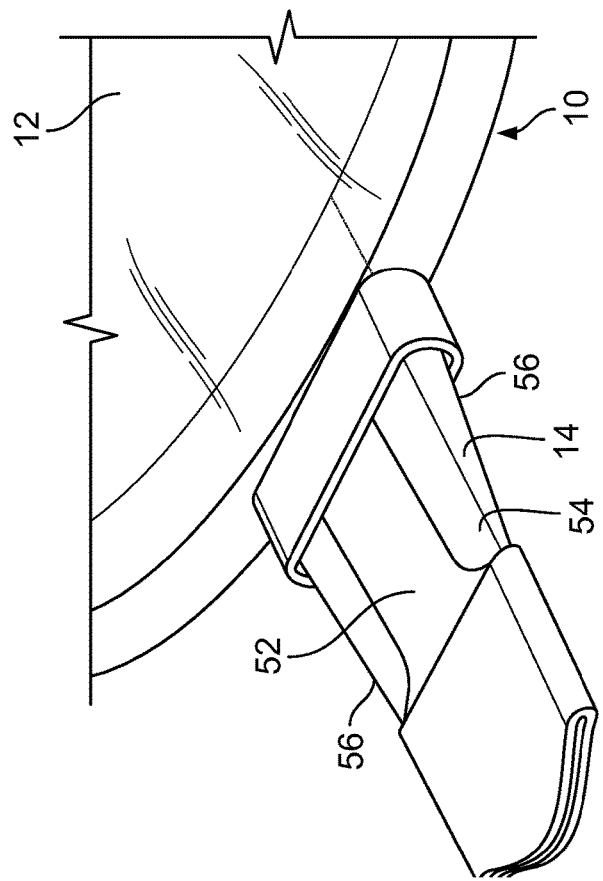
FIG. 12 is a perspective view showing the retractable outlet of FIG. 11 in a first position.
Figure 11:
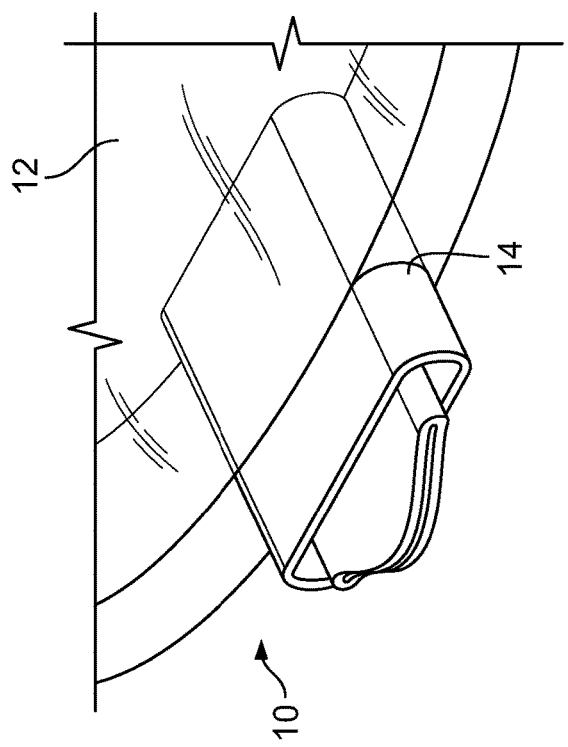
FIG. 11 is a perspective view of a retractable outlet in an open condition according to an embodiment described herein.
Figure 13:
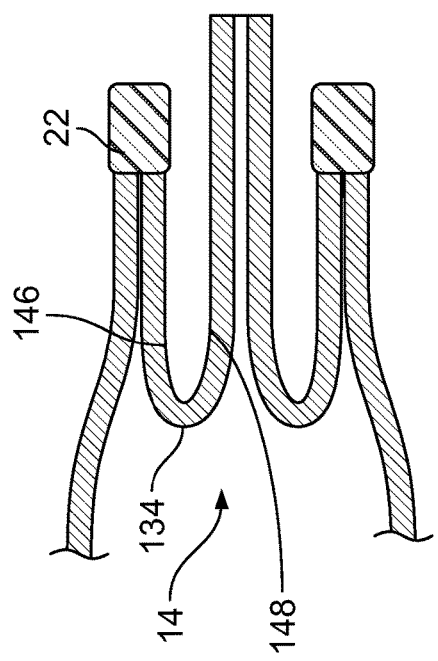
FIG. 13 is a cross-sectional view of the retractable outlet of FIGS. 11 and 12.

FIGS. 11 and 12 show a retractable outlet 14 in the first position (FIG. 11) and the second position (FIG. 12) according to an embodiment described herein. FIG. 13 shows a cross-section of the retractable outlet 14 of FIGS. 11 and 12. Referring to FIGS. 11-13, in one embodiment, the retractable outlet 14 may be formed in a two-layer configuration at or near a position of the first closure 22. In the two-layer configuration, a first layer 146 may be secured to the collection pouch 12 and extend into the collection pouch 12 in the first position. The first layer 146 may be folded over at a bend 134 to form second layer 148 which extends outwardly from the collection pouch 12.

With further reference to FIGS. 11-13, and in particular, FIG. 12, the retractable outlet 14 may be formed having sections of different strength or flexibility to achieve desired bending and/or folding characteristics during movement between the first position and the second position. For example, in one embodiment, the retractable outlet 14 may include a strengthened, rigid or semi-rigid section 52 and a flexible section 54. The semi-rigid section 52 may be formed having an increased material or wall thickness relative to adjacent areas of the outlet 14, such as the flexible section 54, or have another material secured thereto to increase strength and rigidity. For example, the rigid or semi-rigid section 52 may have a foil or foil-like material, such as a metallic foil attached thereto. The semi-rigid section 52 provides sufficient rigidity in the retractable outlet 14 to allow for desired pushing and pulling of the outlet 14 to move between the first and second positions.

In one embodiment, the semi-rigid section 52 may be formed on oppositely facing generally flat surfaces of the retractable outlet 14. By forming the semi-rigid section 52 over a generally or substantially flat area, the semi-rigid section 52 may still buckle so as to bend or roll during movement between the first and second positions. In addition, for movement between the first and second positions, a user may apply opposing laterally inward directed forces to cause the semi-rigid section or sections 52 to elastically bend, increasing longitudinal rigidity during this time.

The soft or flexible section or sections 54 may be formed by having a reduced material or wall thickness relative to the adjacent semi-rigid section 52 of the retractable outlet 14 or by being formed of a material having reduced rigidity or strength relative to the semi-rigid section 52 of the outlet 14. In one embodiment, the flexible section 54 may be formed, for example, along opposed lateral edges 56 and may extend as curved or angled sections on the edges 56. Accordingly, the lateral edges 56 may bend or roll so as to fold over themselves during movement of the retractable outlet 14 between the first and second positions. As such, when moving from the first position to the second position, the retractable outlet 14 may reverse, or turn itself "inside out."

Figure 14:
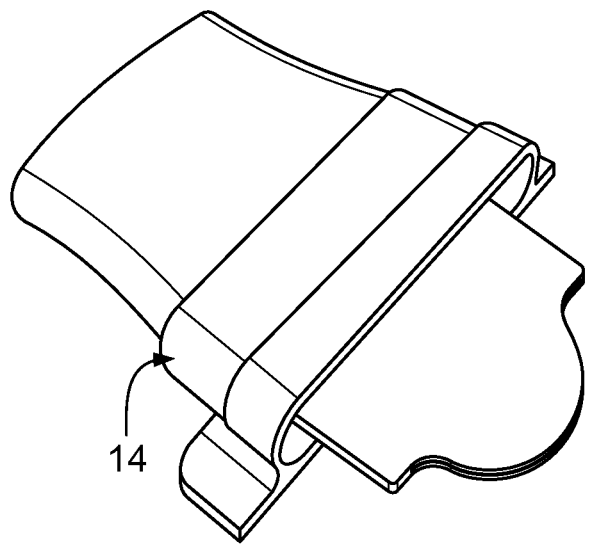
FIG. 14 is a perspective view of a retractable outlet in a first position according to an embodiment described herein.
Figure 15:
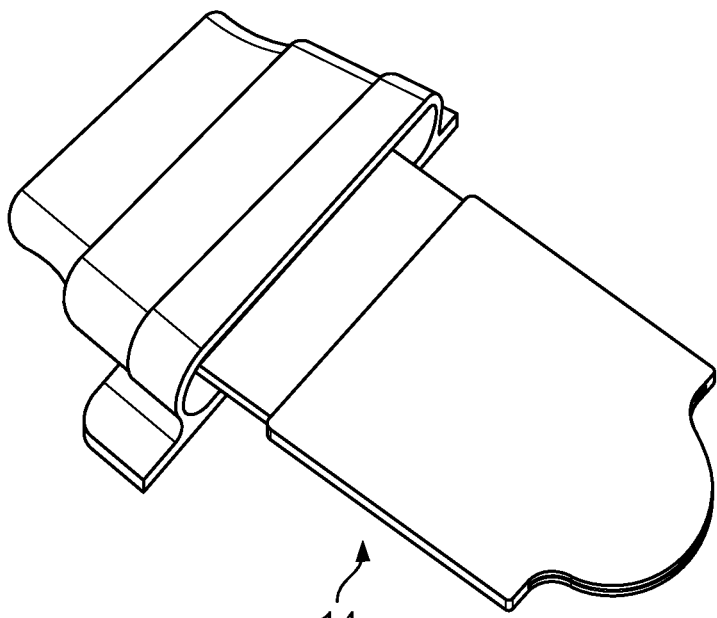
FIG. 15 is a perspective view of the retractable outlet of FIG. 14 in a second position.

FIGS. 14-20 show different views of the retractable outlet 14. FIGS. 14 and 15 show the retractable outlet 14 in positions corresponding to the first position and second position, respectively. In one embodiment, the retractable outlet 14 may be made as a continuous one-piece construction in a molding process. The outlet 14 may be made from, for example, silicone or other similar, suitable polymers.

Figure 16:
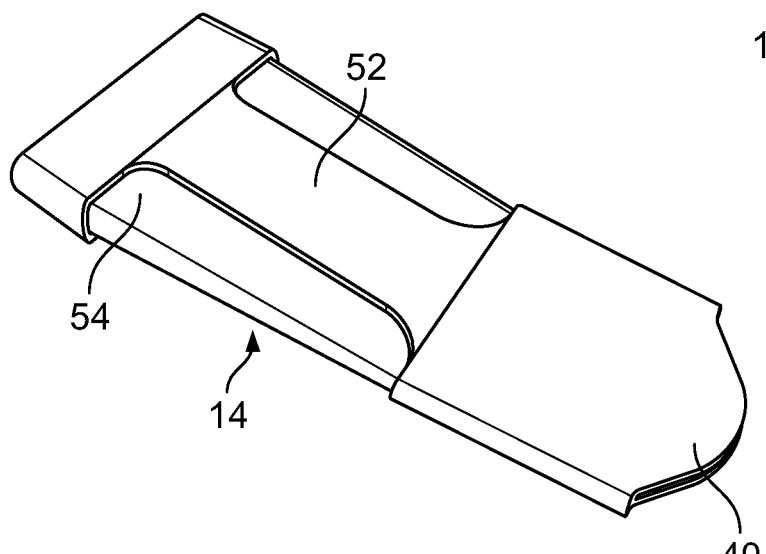
FIG. 16 is a perspective view showing a retractable outlet after manufacture according to an embodiment described herein.
Figure 17:
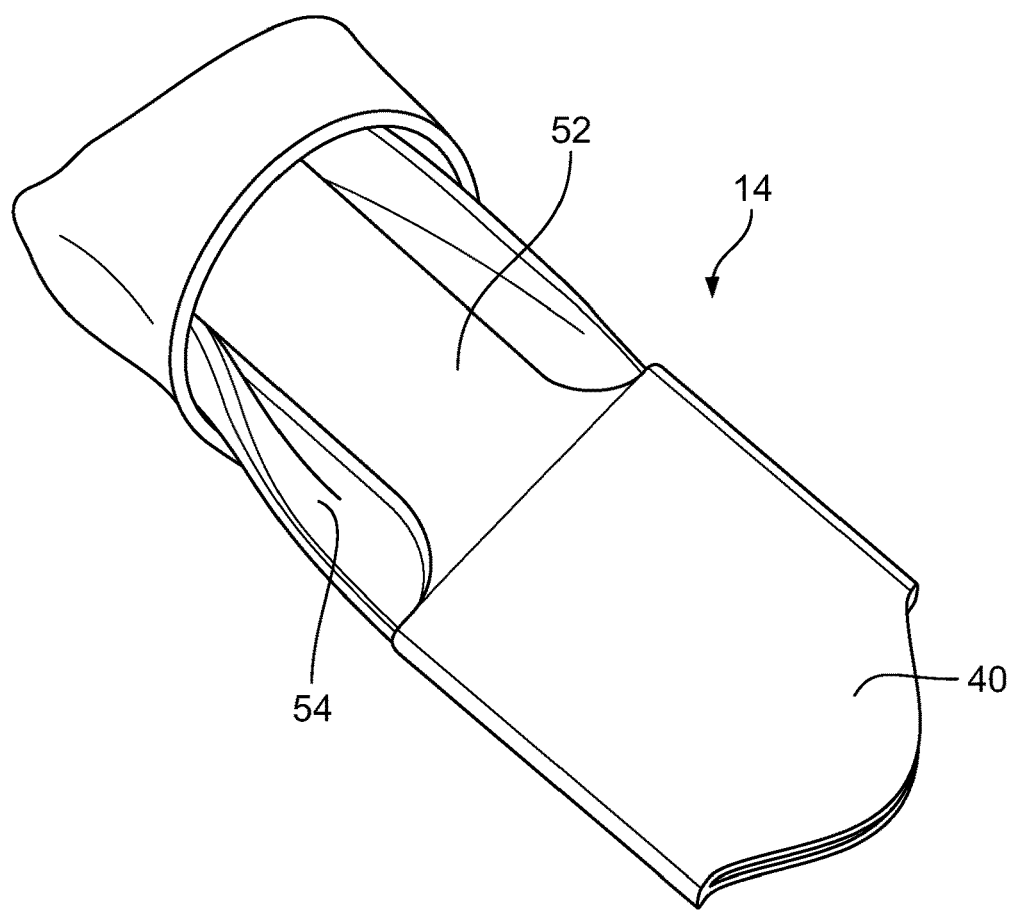
FIG. 17 is a perspective view showing the retractable outlet of FIG. 16 being prepared for installation in an ostomy pouch.

FIG. 16 shows the retractable pouch 14 after removal from a mold, according to an embodiment described herein. As shown in FIG. 16, the retractable outlet 14 may be formed in the mold to have the semi-rigid section 52, flexible section 54 and grip 40. FIG. 17 shows the retractable outlet 14 folded over on an end configured for attachment to the collection pouch, to obtain a desired geometry of the outlet 14.

Figure 18:
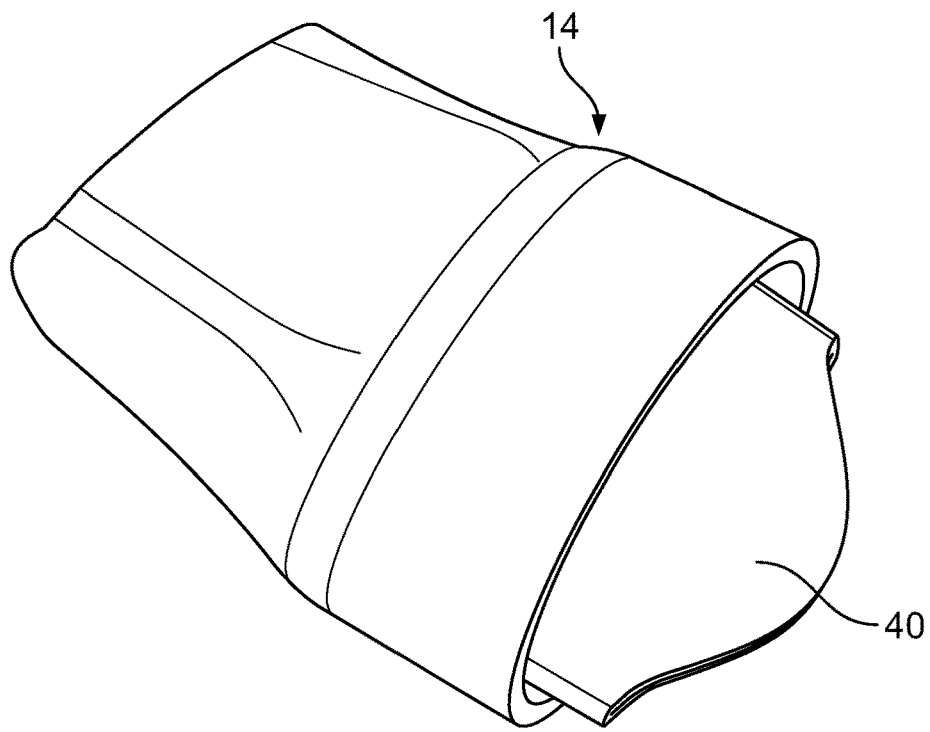
FIG. 18 is a perspective view of the retractable outlet of FIGS. 16 and 17 in a first position prepared for installation in an ostomy pouch.
Figure 19:
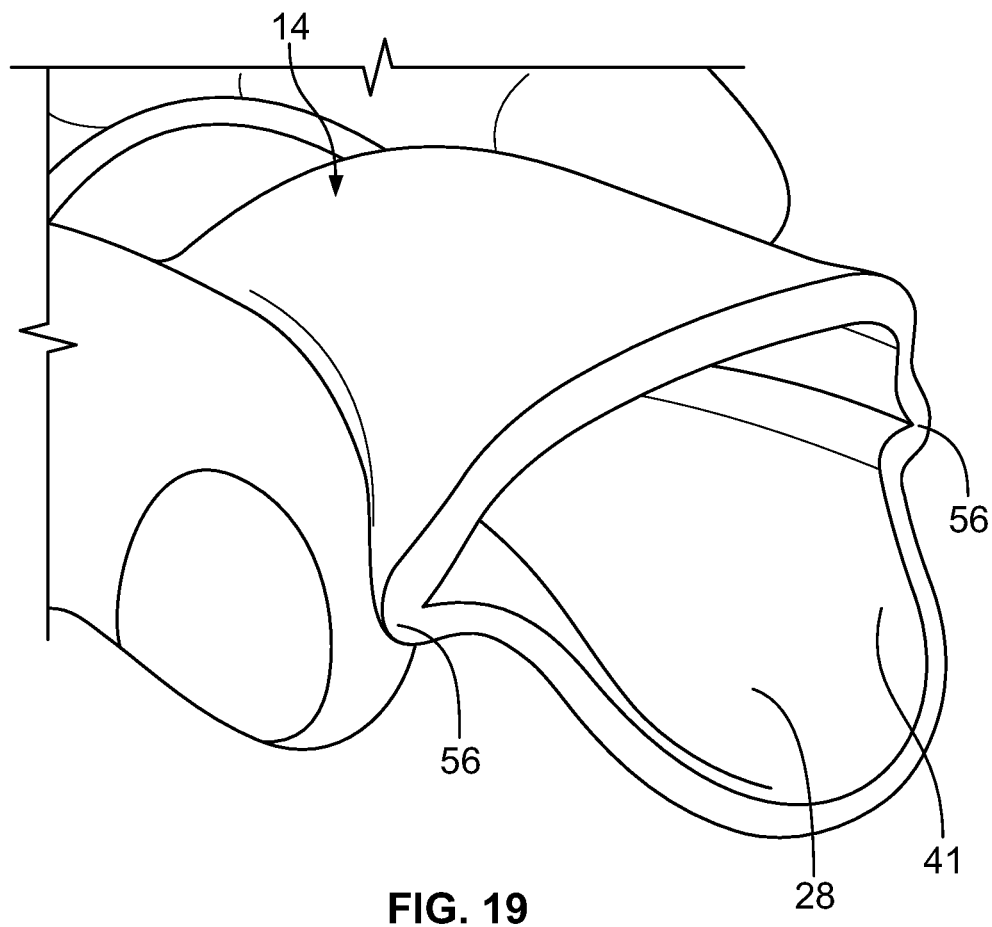
FIG. 19 is a perspective view of the retractable outlet of FIGS. 16-18 in an open condition.

FIG. 18 shows the retractable outlet 14 in a position corresponding to the first position with the outlet 14 closed, according to an embodiment described herein. It is understood that a height (or width measured across internal opening or flow path) may be defined by a geometry of the first closure 22 on the collection pouch 12 (see FIGS. 1, 2 and 5, for example). FIG. 19 shows the retractable outlet 14 in an open condition, in response to application of opposing inwardly directed forces to opposite lateral edges 56 thereof.

Figure 20:
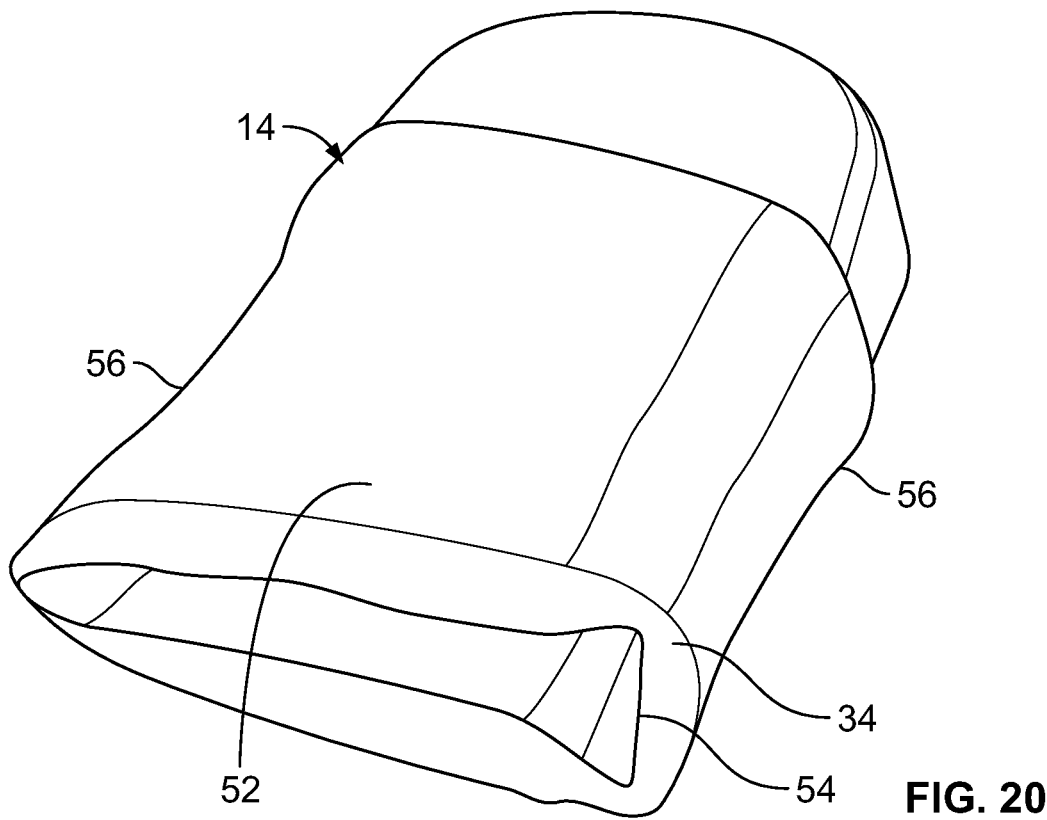
FIG. 20 is a perspective view of an end of a retractable outlet to be received in an ostomy pouch according to an embodiment described herein.

FIG. 20 shows an end of the retractable outlet 14 configured for insertion into the collection pouch 12, according to one embodiment described herein. Referring to the example in FIG. 20, the semi-rigid section 52 may fold or curl over itself at the bend 34 during movement between the first and second positions. Similarly, the flexible section 54 may stretch so as to allow bending or folding of the lateral edges 56 during movement between the first and second positions.

Figure 21:
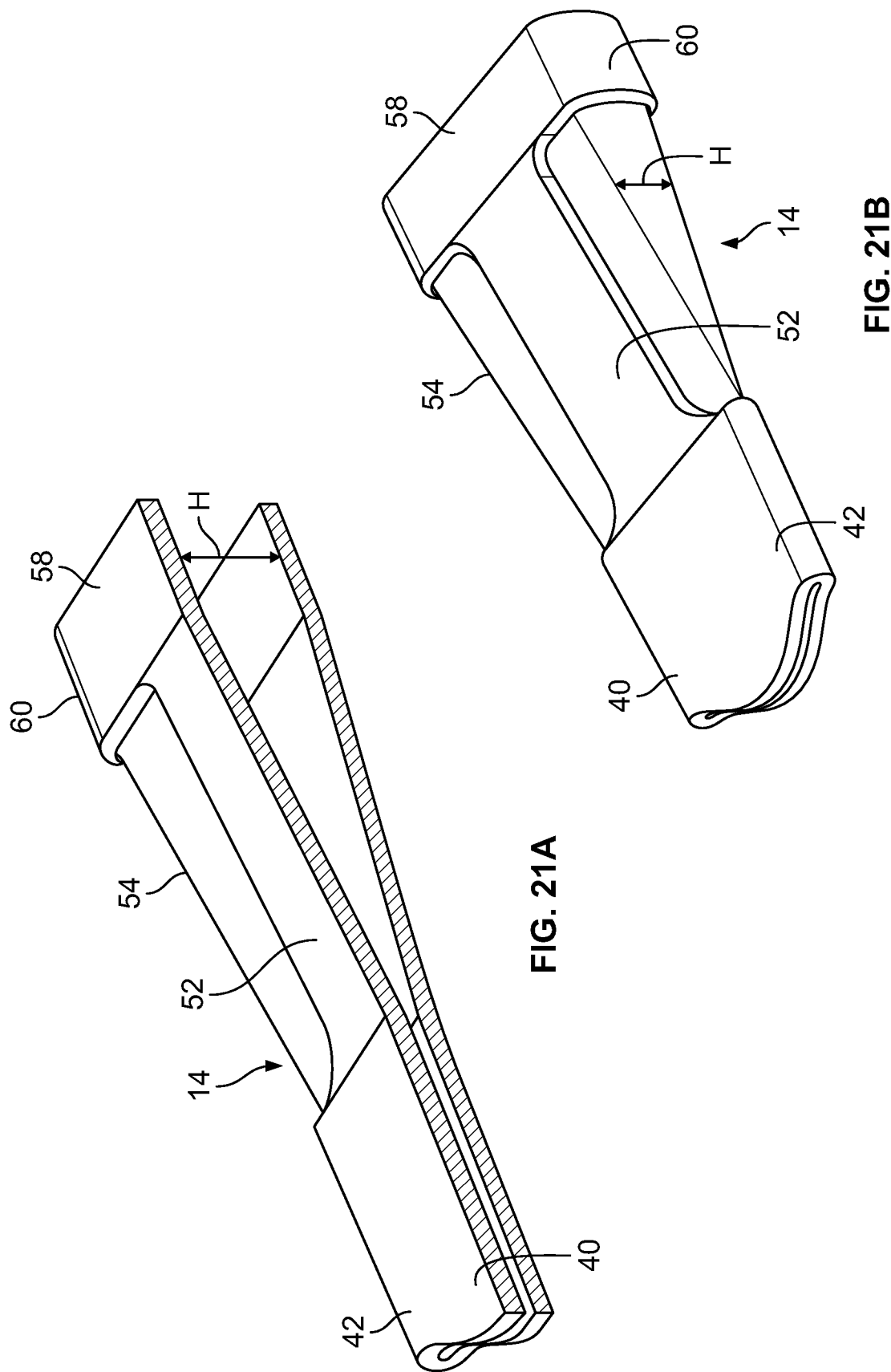
FIGS. 21A-B are a section view and a perspective view of a retractable outlet according to an embodiment described herein.

FIGS. 21A-B are a section view and a perspective view showing geometries of a retractable outlet 14 according to an embodiment described herein. With reference to FIGS. 21A-B, the retractable outlet 14 may include a first, proximal end 58 and the second, distal end 42. The proximal end 58 may be secured to the collection pouch 12 generally in the region of the first closure 22 (see, for example, FIGS. 1, 2, 5 and 6). The proximal end 58 may also have a collar 60. In addition, a height H of the retractable outlet 14 may decrease moving from the first end 58 to the second end 42. That is, the outlet 14 may taper inwardly toward the second end 42. In one embodiment, the height H may be substantially constant at the collar 60 and decrease moving toward the grip 40. The height H may be substantially constant along the grip 40 in the closed condition. The height H in the grip 40 may be increased in the opened condition so allow waste to flow from the retractable outlet 14.

Still referring to FIGS. 21A-B, in one embodiment, the collar 60 may have a material thickness of about 2.0 mm. The flexible section 54 may have a thickness of about 0.5 mm. The semi-rigid section 52 and grip 40 may have a material thickness of about 2.0 mm. The grip 40 may be formed with a SLS core of about 0.8 mm. However, these dimensions are provided for the purposes of example only, and the present disclosure is not limited to these dimensions. It is apparent to those having ordinary skill in the art that the retractable outlet may be formed having different dimensions so long as the retractable outlet retains the functionality and/or characteristics described herein.

Figure 22:
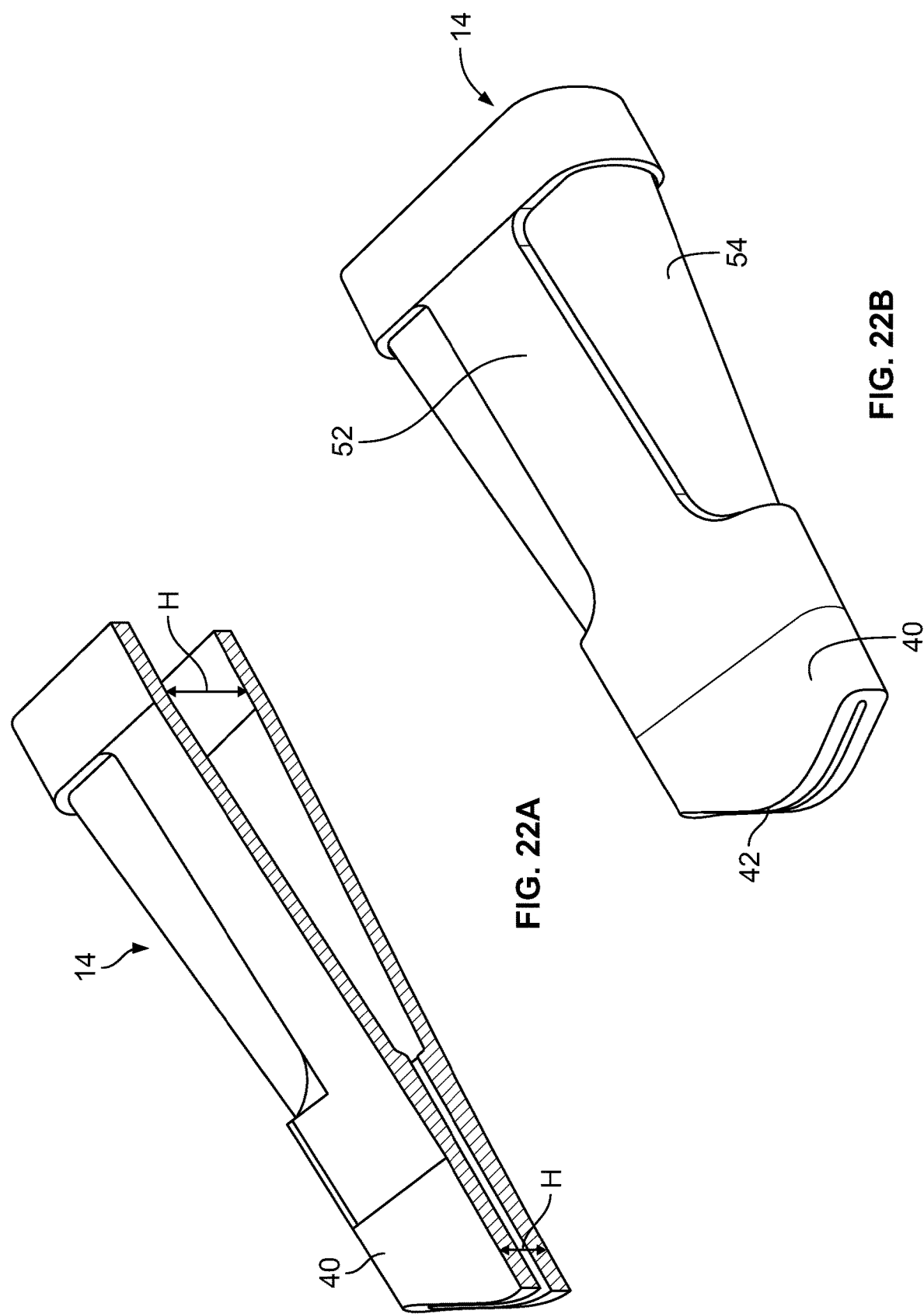
FIGS. 22A-B are a section view and a perspective view of a retractable outlet according to an embodiment described herein.

FIGS. 22A-B are a section view and a perspective view showing geometries of a retractable outlet 14 according to another embodiment described herein. The retractable outlet 14 of FIGS. 22A-B may be formed similarly to that of FIGS. 21A-B. However, in the embodiment shown in FIGS. 22A-B, a height H of the grip 40 may decrease in a direction toward the second, distal end 42, along at least a portion of the grip 40. For example, in one embodiment, the retractable outlet 14 may have a height H of approximately 7.0 mm where the semi-rigid section 52 meets the grip 40. The height H may decrease to about 5.0 mm along the grip 40 in a direction toward the second end 42. A remainder of the grip 40 may be formed having a substantially constant height H. In addition, the grip 40 may be formed with a milled core, and foil may be added to the core to increase rigidity. It is understood that these dimensions are provided for the purposes of example only, and the present disclosure is not limited to dimension. It is apparent to those having ordinary skill in the art that the retractable outlet 14 may be formed having different dimensions so long as the retractable outlet 14 retains the functionality and/or characteristics described herein.

Figure 23:
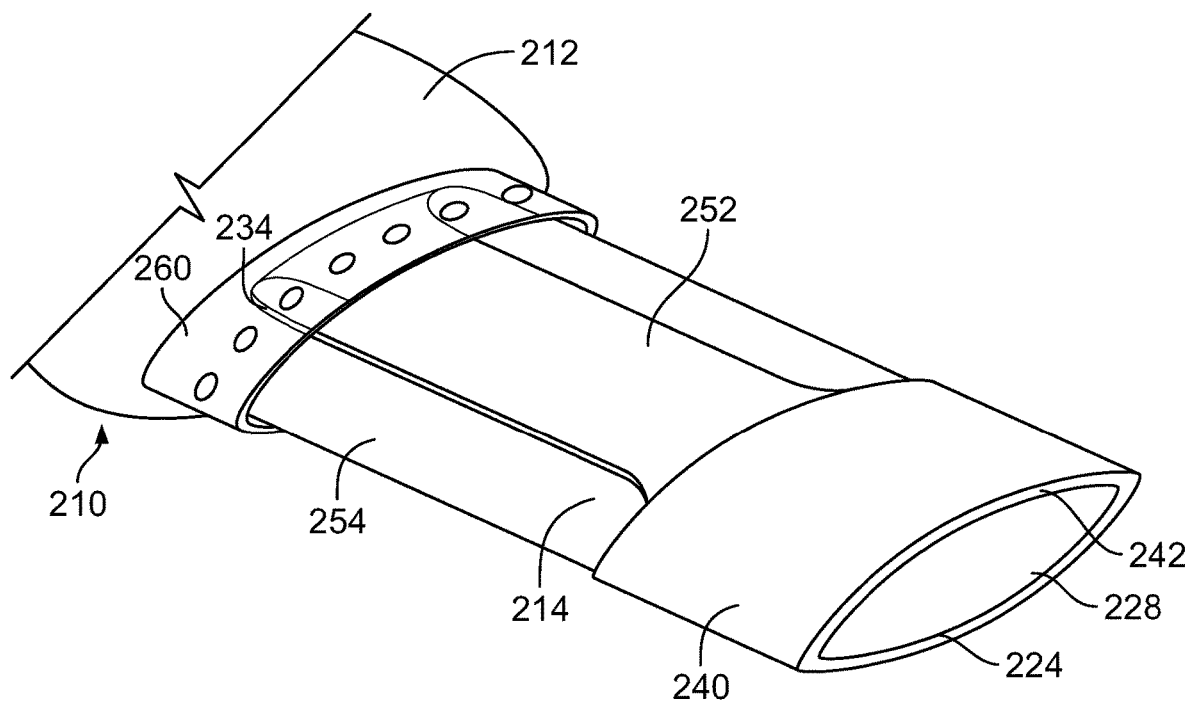
FIG. 23 is a perspective view of a portion of an ostomy pouch having a retractable outlet in a second position according to an embodiment described herein.
Figure 24:
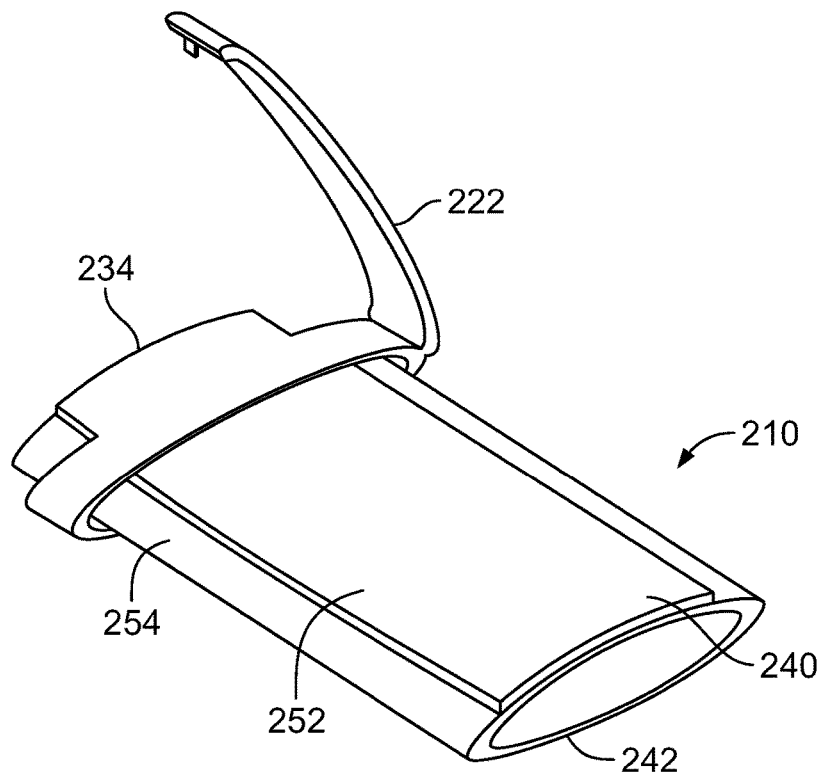
FIG. 24 is a perspective view showing a retractable outlet in a first position according to an embodiment described herein.

FIGS. 23 and 24 show an ostomy pouch 210 having a collection pouch 212 and retractable outlet 214 according to another embodiment described herein. With reference to FIGS. 23 and 24, the retractable outlet 214 includes an internal passageway 228 may also include a semi-rigid section 252, a flexible section 254 and a grip 240. The semi-rigid section 254 and the grip 240 may be formed having substantially the same material or wall thickness, and the flexible section 254 may have a reduced material or wall thickness relative to the semi-rigid section 252 and the grip 240.

The ostomy pouch 210 may also include a collar 260 that may serve as a weld zone for attachment of the retractable outlet 214 to the collection pouch 212 and/or attachment of a first closure 222 to the collection pouch 212 or retractable outlet 214. The collar 260 may be formed integrally and continuously as one piece with the retractable outlet 214. Alternatively, the retractable outlet 214 may be attached to the collar 260 using known fastening techniques, such as heat sealing, welding, or the like. A second closure 224 may be included at or near the distal end 242 of the outlet 214 to close the internal passageway 228.

In the first, retracted position, the retractable outlet 214 is retracted into the collection pouch 212 and extends to a first distance D1 from a collection pouch opening 230, with the grip 240 remaining outside of the collection pouch 212. In one embodiment, the retractable outlet 214 includes a bend or fold 234 that moves within the collection pouch 212 when moving the retractable outlet 214 between the first and second positions. In the first position, the bend 234 is positioned at the first distance D1 and in the second position, the bend 234 is positioned a second distance D2 from the collection pouch opening 230, less than the first distance D1. However, the bend 230 remains in the collection pouch 212 with the outlet 214 in the second position. That is, the retractable outlet 214 is not completely reversed or inverted when moved first position to the second position.

Referring to FIG. 24, the retractable outlet 214 may alternatively be formed having a semi-rigid section 252 and a grip 240 that are uniform in width with one another. In this embodiment, the flexible section 254 may extend completely to the distal or second end 242 of the retractable outlet 214 and separate opposite sides of the grip 240.

Figure 25:
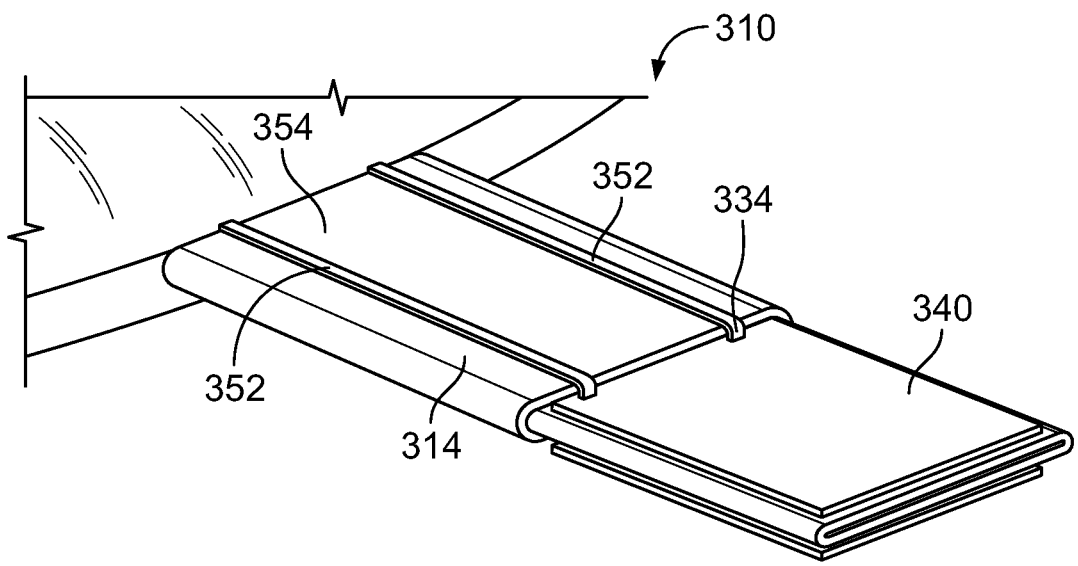
FIG. 25 is a perspective view of a portion of an ostomy pouch having a retractable outlet according to an embodiment described herein.
Figure 26:
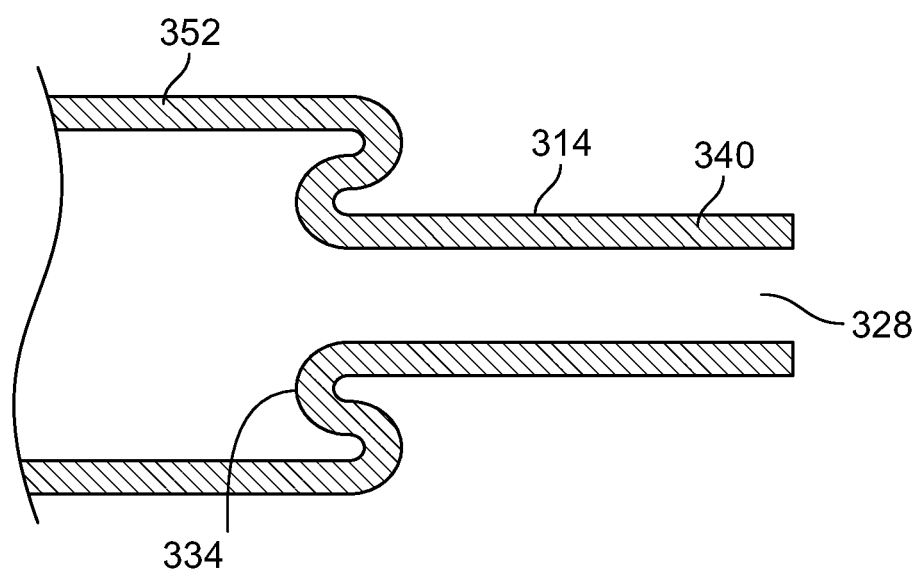
FIG. 26 is a side view of the retractable outlet of FIG. 25.

FIGS. 25 and 26 show an ostomy pouch 310 having a collection pouch (not shown) and a retractable outlet 314 according to another embodiment described herein. In this embodiment, a strengthened or semi-rigid section 352 of the retractable outlet 314 may be formed as one or more ribs 352 extending along at least a portion of a length of the retractable outlet 314. The retractable outlet 314 also includes a flexible section 354 may be at least partially supported by the one or more ribs 352. Further, the retractable outlet 314 includes a semi-rigid grip 340 that may extend from one end of the one or more ribs 352 and the flexible section 354 to be grasped by a user. An internal passageway 328 is defined in the retractable outlet 314, including the grip 340. In one embodiment, the one or more ribs 352 include two spaced apart ribs 352. The ribs 352 are configured to curl around a corner 334 during retraction into the collection pouch (not shown).

Figure 27:
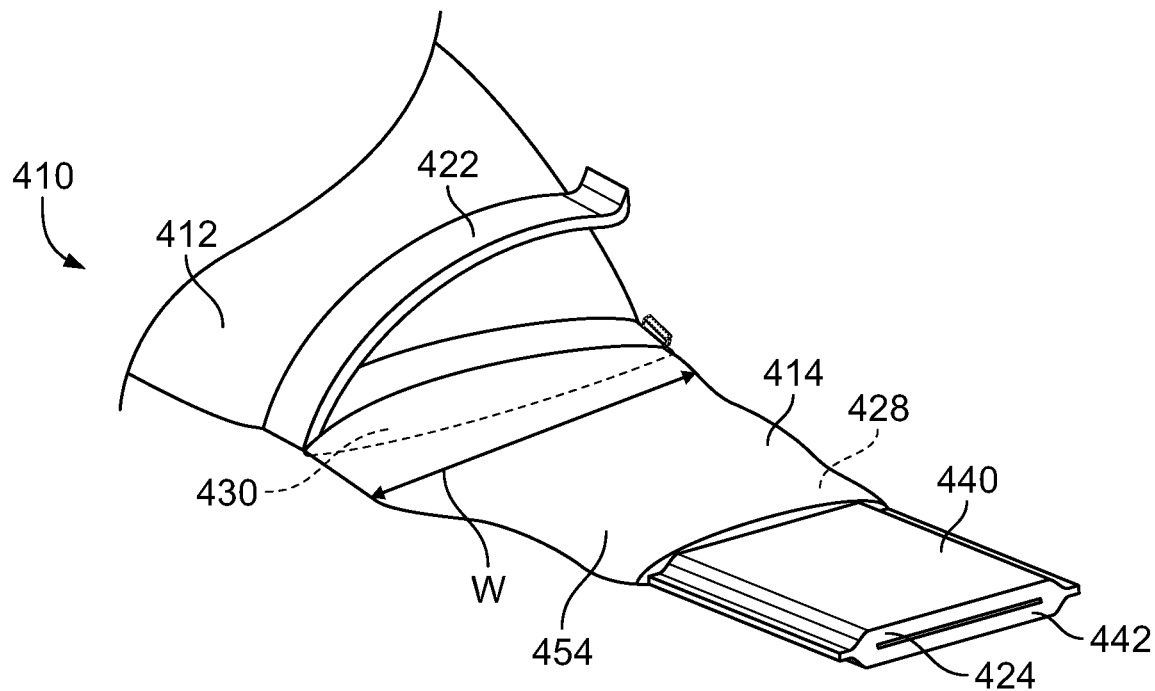
FIG. 27 is a perspective view of a portion of an ostomy pouch having a retractable outlet in a second position according to an embodiment described herein.

FIG. 27 shows an ostomy pouch 410 having a collection pouch 412 and a retractable outlet 414 according to another embodiment described herein. In one embodiment, the retractable outlet 414 may be formed substantially as a flexible section 454, having a semi-rigid grip 440 disposed on a distal end 442. The flexible section 454 may be formed without any reinforced or strengthened sections, and may be made from a relatively thin, soft and flexible material. The semi-rigid grip 440 may be formed substantially as described above. An internal passageway 428 extends through the retractable outlet 414 and a second closure 424 is positioned at the distal end 442, for example, at the grip 440. The retractable outlet 414 may be connected to the collection cavity 420 of the collection pouch 412 by way of a relatively large discharge opening 430. A first closure 422 may selectively open and close the opening 430. In one embodiment, the first closure 422 may be a clamp or similar closure to sealingly close the discharge opening 430. Further, in one embodiment, a width W of the retractable outlet 414 may decrease in a direction from the opening 430 to the grip 440.

Figure 28:
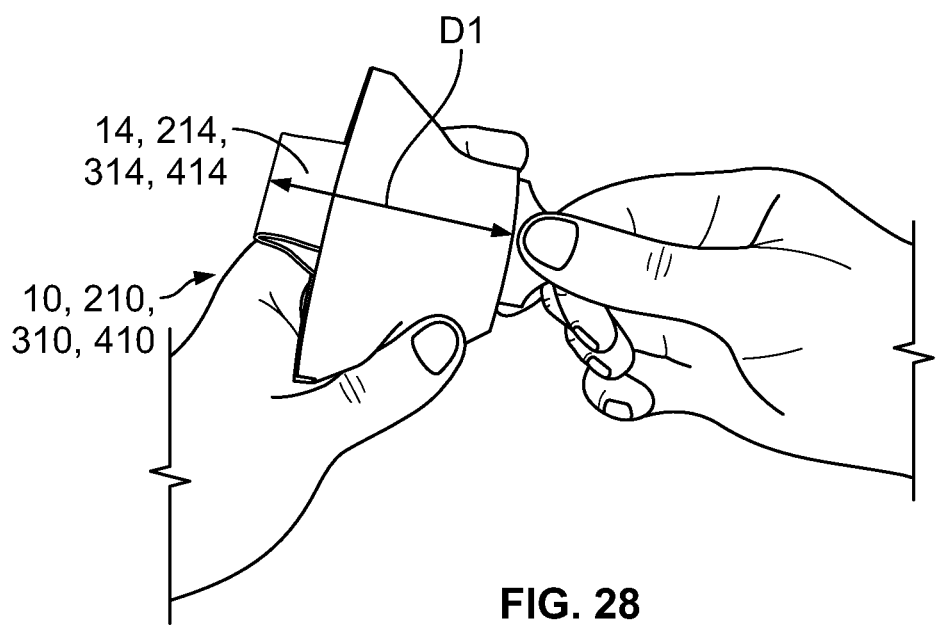
FIG. 28 is a perspective view showing a portion of an ostomy pouch having a retractable outlet in a first position according to an embodiment described herein.
Figure 29:
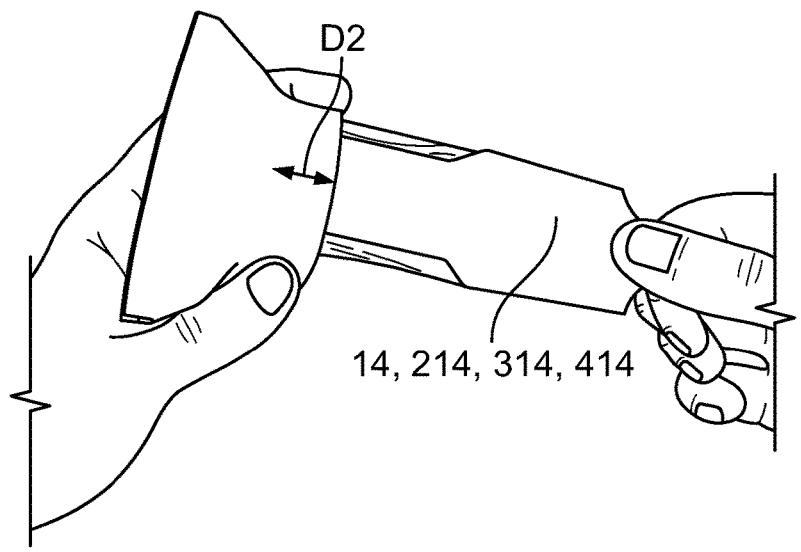
FIG. 29 is a perspective view showing a portion of the ostomy pouch of FIG. 28 having a retractable outlet in a second position according to an embodiment described herein.

FIGS. 28-31 show an example of the ostomy pouch 10, 210, 310, 410 described herein in different stages of use, with the retractable outlet 14, 214, 314, 414 moving between the first and second positions. FIG. 28 shows an example of the retractable outlet 14, 214, 314, 414 in the first position, retracted into a collection pouch 12, 212, 412, which is partially cut away for clarity. In the first position, the retractable outlet 14, 214, 314, 414 extends a first distance D1 in the collection pouch 12, 212, 412. FIG. 29 shows the retractable outlet 14, 214, 314, 414 in the second position, extended from the collection pouch 12, 212, 412. In the second position, the retractable outlet 14, 214, 314, 414 extends either a second distance D2 less than the first distance D1 in the collection pouch 12, 212, 412, or extends completely out of the collection pouch 12, 212, 412.

Figure 30:
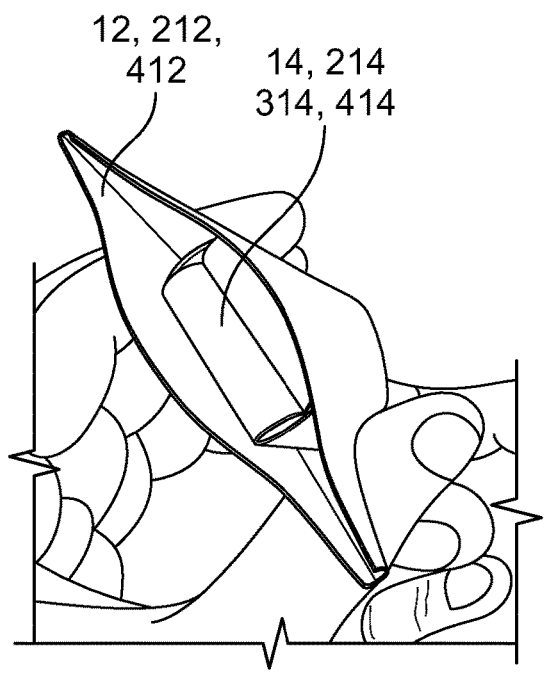
FIG. 30 is an interior view of the ostomy pouch of FIGS. 28 and 29 having a retractable outlet in a second position according to an embodiment described herein.
Figure 31:
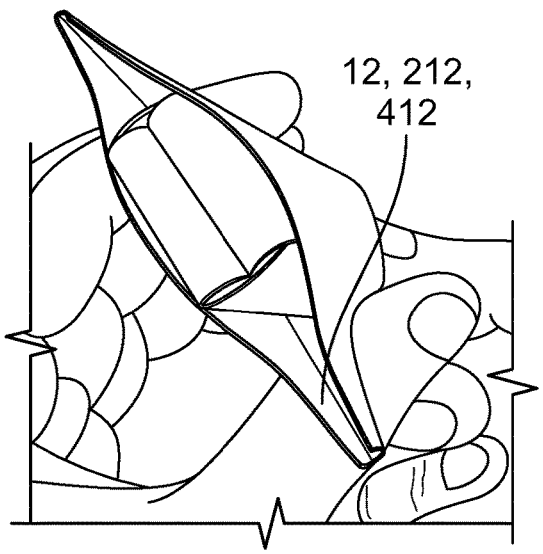
FIG. 31 is an interior view of the ostomy pouch of FIGS. 28-30 having a retractable outlet in a first position according to an embodiment described herein.

FIG. 30 shows an example of the retractable outlet 14, 214, 314, 414 moved toward the second position, from within a cut away section of the collection pouch 12, 212, 412, for clarity. FIG. 31 shows the retractable outlet 14, 214, 314, 414 moved toward the first, retracted position, from within a cut away section of the collection pouch 12, 212, 412, according to one embodiment.

In the embodiments above, a retractable outlet may be moved between a first position retracted within a collection pouch and a second position extending from the collection pouch. The retractable outlet is connected a collection cavity of the collection pouch by a first discharge opening so that waste may be received in the retractable outlet from the collection cavity, with the retractable outlet in the second position. A second discharge opening is included at a distal end of the retractable outlet to allow for drainage of waste from the ostomy pouch.

The ostomy pouch in the embodiments above includes a closure. The closure may be a first closure configured to serve as a primary closure in normal daily use of the ostomy pouch. That is, the first closure may close and seal the collection pouch with the retractable outlet in the first position, so that bodily waste may be received and held in the collection cavity of the collection pouch. Said differently, the first closure may close and/or seal the first discharge opening. It is understood that with the retractable outlet in the first position, the first closure also substantially prevents leakage of contents from the retractable outlet by closing the first discharge opening that connects the collection cavity to the retractable outlet. In addition, with the retractable outlet in the second, extend position, the first closure may be closed to separate the collection cavity from the internal passageway of the retractable outlet so that the retractable outlet may be cleaned while additional bodily waste may be concurrently received in the collection pouch. Further, the first closure may serve as a closure mechanism to a night drainage system. For example, with the retractable outlet in the second position, the first closure may connect or couple to a night drainage system for extended, overnight use of the ostomy pouch with the night drainage system.

Alternatively, the closure may be a second closure positioned on the retractable outlet. The second closure is configured to selectively open and close the internal passageway of the retractable outlet and allow for drainage of the collection cavity via the retractable outlet. The second closure may be disposed at a distal end of the retractable outlet and in some embodiments, in the closed condition, may seal the distal end of the internal passageway. That is, the second closure may close or seal the second discharge opening. In some embodiments, the second closure may be connected or coupled to a night drainage system for extended, overnight use of the ostomy pouch with the night drainage system. In another embodiment, the ostomy pouch includes both the first closure and second closure described above.

In the course of normal daily use, according to one embodiment, the retractable outlet is retracted into the collection pouch and the second closure may be embedded inside the first closure. When emptying the pouch, the first closure is opened and the retractable outlet is extended. The second closure may be separated or opened to allow for drainage of the pouch. The first closure may then be closed, with the retractable outlet in the second position, and the internal passageway of the retractable outlet may then be cleaned without interference of continuous waste or fluid output. In one embodiment, the first closure may be a clamp and the second closure may be one or more closing members, such as releasable fasteners or spring-biased closures.

Accordingly, in embodiments above, by providing first and second independent closures, a retractable outlet may be cleaned without interference from continuous waste and/or fluid output. In addition, the retractable outlet member may be discretely stored without repeated folding. In other embodiments, a single closure may substantially prevent or limit leakage of the contents from the collection cavity and/or the retractable outlet.

It is understood that individual features the embodiments above may be combined with or replace certain features in different embodiments described above. In addition, it is understood that further description of some features in certain embodiments above may be omitted where the feature(s) are described in another embodiment. Further still, it understood that similar features across the embodiments may be referred to with similar terminology and/or reference numbers.

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

The invention claimed is:

1. An ostomy pouch comprising:
   a collection pouch having a first side wall and a second side wall joined along a periphery to define an internal collection cavity for containing body waste, the collection pouch including an outlet opening;
   a retractable outlet formed separately from the collection pouch and attached to the collection pouch at the outlet opening, the retractable outlet including an internal passageway connected to the collection cavity, the retractable outlet being movable between a first position and a second position, wherein the retractable outlet is retracted to at least in part within the collection cavity in the first position and extending outwardly from the collection cavity in the second position;
   a discharge opening formed at a distal end of the retractable outlet; and a closure configured to selectively allow or prevent discharge of a waste material from the collection cavity or the retractable outlet.

2. The ostomy pouch of claim 1, wherein the closure is positioned on the collection pouch and is configured to selectively allow or prevent discharge of a waste material from the collection cavity.

3. The ostomy pouch of claim 2, wherein the closure is a clamp fastened around an exterior of the first and second side walls.

4. The ostomy pouch of claim 3, wherein the clamp clamps the first and second sidewalls and the outlet.

5. The ostomy pouch of claim 2, wherein the closure is configured for connection to a night drainage system.

6. The ostomy pouch of claim 1, wherein the closure is positioned on the retractable outlet and is configured to selectively allow or prevent discharge of a waste material from the discharge opening.

7. The ostomy pouch of claim 6, wherein the closure is a spring biased closure.

8. The ostomy pouch of claim 7, wherein the spring biased closure biases opposing side walls of the retractable outlet toward one another.

9. The ostomy pouch of claim 6, wherein the closure includes one or more releasable closing members.

10. The ostomy pouch of claim 6, wherein the closure is configured for connection to a night drainage system.

11. The ostomy pouch of claim 1, the collection pouch further comprising a neck portion and the retractable outlet is connected to the neck portion.

12. The ostomy pouch of claim 1, wherein with the retractable outlet in the second position, an interior passageway of the outlet is connected to the internal collection cavity.

13. The ostomy pouch of claim 1, wherein the retractable outlet is formed by one or more walls, and the one or more walls are reversible when moving from the first position to the second position and vice versa.

14. The ostomy pouch of claim 1, wherein the retractable outlet includes a semi-rigid section and a flexible section.

15. The ostomy pouch of claim 1, wherein in the first position, the retractable outlet forms a non-return valve preventing leakage of waste material from the collection cavity.

16. The ostomy pouch of claim 1, wherein the closure is a first closure configured to selectively allow or prevent discharge of a waste material from the collection cavity, and the ostomy pouch further comprises a second closure configured to selectively allow or prevent discharge of the waste material from discharge opening.

* * * * *